United States Patent [19]

Reed

[11] Patent Number: 5,332,665
[45] Date of Patent: Jul. 26, 1994

[54] SPECIES SPECIFIC, HIGH AFFINITY MONOCLONAL ANTIBODIES

[75] Inventor: Guy L. Reed, Winchester, Mass.

[73] Assignee: The General Hospital Corporation, Boston, Mass.

[21] Appl. No.: 31,019

[22] Filed: Mar. 11, 1993

Related U.S. Application Data

[63] Continuation of Ser. No. 809,175, Dec. 18, 1991.

[51] Int. Cl.$^5$ .................... A61K 35/16; C07K 15/28
[52] U.S. Cl. .......................... 435/70.21; 435/172.2; 435/240.27; 530/388.1; 530/388.25; 530/389.1
[58] Field of Search ............ 435/70.21, 172.2, 240.27; 530/388.25, 389.1, 388.1

[56] References Cited

PUBLICATIONS

1990 Catalog Sigma Immunochemicals Sigma Co.
Current Protocols in Molecular Biology 11.0.3–11.3.1 1988.
Yelton et al. *Hybridoma* 1(1):5–11 1981.
Buchner and Rudolph, *Bio/Technology* 9:157–162 (1991).
Davis, et al., *Bio/Technology* 9:165–169 (1991).
Kennedy, et al., *Clinica Chimica Acta* 70:1–31 (1976).
Kohler et al., *Eur. J. Immunol.* 6:511–519 (1976).
Kohler et al., *Nature* 256:495–497 (1975).
Mudgett-Hunter et al., *Molecular Immunology* 22(4):477–488 (1985).
Reed et al., *Proc. Natl. Acad. Sci. USA* 87:1114–1118 (1990).
Ware et al., *Journal of Immunological Methods* 74:93–104 (1984).

Primary Examiner—George C. Elliott
Assistant Examiner—Donald E. Adams
Attorney, Agent, or Firm—Sterne, Kessler, Goldstein & Fox

[57] ABSTRACT

High affinity species specific monoclonal antibodies are provided. The antibodies are anti-immunoglobulin antibodies which bind the Ig of a particular species but does not cross react with the Ig of another species. Methods for making and using the antibodies of the invention are provided.

5 Claims, 4 Drawing Sheets

| 106 ▸
| 80 ▸

| 50 ▸

| 33 ▸
| 27 ▸

SPECIES SPECIFIC, HIGH AFFINITY MONOCLONAL ANTIBODIES

This invention was made with government support under Grant HL02348 awarded by the National Institutes of Health. The government has certain rights in the invention.

This application is a continuation of application Ser. No. 07/809,175, filed Dec. 18, 1991.

FIELD OF THE INVENTION

The present invention relates to anti-immunoglobulin antibodies for use in vitro and in vivo.

BACKGROUND OF THE INVENTION

Secondary-anti-(mouse immunoglobulin) antibodies have long been used to detect the binding of monoclonal antibodies (MAbs) to the target antigens. This is advantageous because it combines the exquisite specificity found in primary MAb with the amplification and versatility allowed by the second antibody reagent. Using specific anti-immunoglobulin antibodies solves many of the difficulties in locating and quantitating antibodies when these molecules are found in complex mixtures of serum or tissue culture proteins.

A concern in the generation of anti-immunoglobulin response is how similar antibodies are from species to species. Because of this extraordinary similarity between the amino add sequence of different species immunoglobulin (Ig), it has been difficult to obtain a secondary, anti-(mouse)Ig antibody preparation which does not also bind to the Ig of other species.

The cross-reactive binding found in anti-immunoglobulin antibodies may create false negative or positive assay results. Thus, experiments performed in serum or other biological fluids have required washing steps or other techniques to remove potentially cross-reactive antibodies before employing the second antibody. Because of the high concentrations present in vivo, this problem of cross reactivity has prevented effective use of a second antibody system for studying primary mouse monoclonal antibodies in animals.

Anti-Ig antibodies are employed in the various number of assays. Accordingly, there is a need for high affinity monoclonal antibodies which are species specific.

RELATED ART

The binding characteristics and partial variable-region primary structure of 15-high monoclonal anti-digoxin antibodies were reported by Mudgett-Hunter et al., Molecular Immunology 22:477–488 (1985).

Ware et al., Journal of Immunological Methods 74:93–104 (1984) describe the immunochemical properties of a rat Mab with specificity for mouse κ-chains by the 187.1.10 hybridoma. The utility of 187.1.10 Mab as a general second antibody reagent for mouse antibodies was discussed.

The principals of receptor binding studies are discussed by Schwarz, K. R. in The Heart and Cardiovascular System, H. A. Fozzard et al. (Ed.) Raven Press, New York (1986) pages 186–188.

SUMMARY OF THE INVENTION

The present invention is drawn to species-specific high affinity monoclonal antibodies or fragments thereof. The antibodies are anti-immunoglobulin (and anti-Ig fragment) antibodies which bind to Ig or Ig fragments of a particular species but which do not cross react with the Ig of other species. Methods for making and using the antibody molecules of the invention are disclosed.

BRIEF DESCRIPTION OF THE FIGURES

FIG. 3. Immunoblot analysis of binding specificity of rat MAbs. Mouse Fab was electrophoresed on 12% polyacrylamide gels and transferred to nitrocellulose. After blocking nonspecific protein binding sites, the nitrocellulose was incubated with various MAbs. The blots were washed and incubated with $^{125}$I-goat antirat antibody. After additional washing the blots were subjected to autoradiography.

DETAILED DESCRIPTION OF THE INVENTION

Figure 1A:
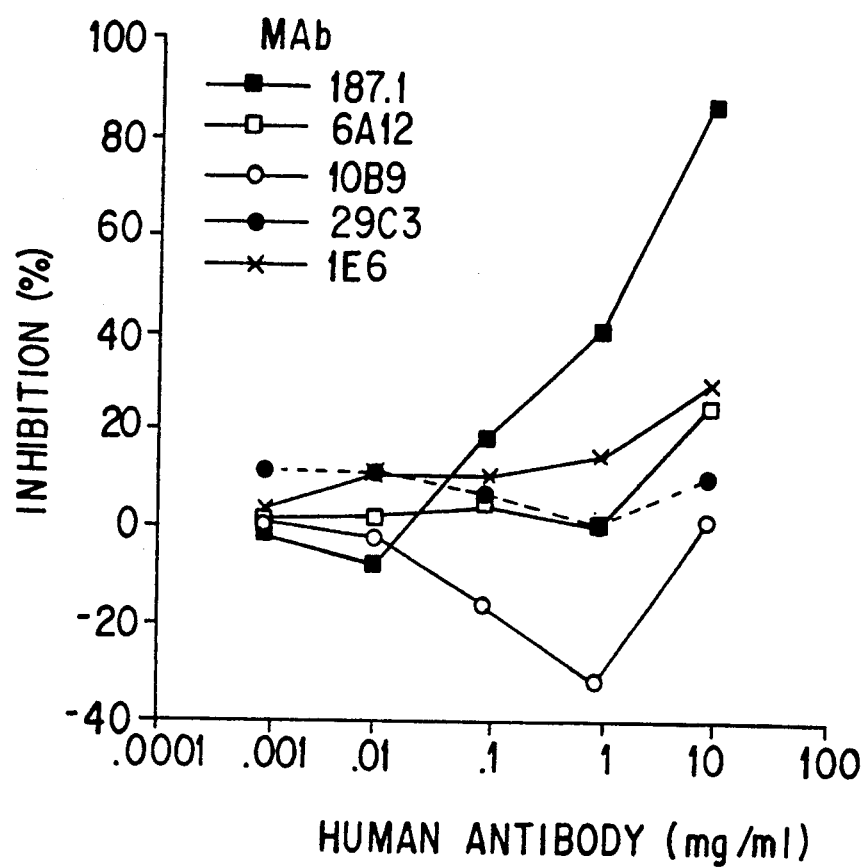
FIGS. 1A and 1B. Inhibition of Binding of rat MAbs to $^{125}$I-mouse Fab by human (FIG. 1A) or rabbit (FIG. 1B) antibody. Rat MAbs were immobilized in wells of a microtiter plate and then incubated with $^{125}$I mouse Fab with varying concentrations of plasma as the source of human or rabbit immunoglobulin. The resulting amount of bound mouse Fab was determined by γ-counting. The percent of inhibition of binding was computed as described in the Methods.

High affinity, species specific monoclonal antibodies and fragments thereof are provided. The monoclonal antibodies are anti-immunoglobulin antibodies which are specific for the Ig or Ig fragments of a particular species. That is, these antibodies do not cross react with antibodies from other species.

The antibodies that bind to other antibodies are secondary antibodies. That is, they bind to antibody or antibody fragments. The bound antibodies are herein called primary antibodies and are capable of binding any antigen.

For the most part the secondary antibodies of the invention bind to the κ chain of the primary immunoglobulins. However, different epitopes may be recognized which are shared by different antibodies.

By "anti-immunoglobulin (and anti-Ig fragment) antibodies is intended antibodies that are directed against immunoglobulins or immunoglobulin fragments. Antibody or immunoglobulin fragments can be generated by enzymatic or recombinant methods. Such fragments can also be utilized to generate species specific antibodies. Therefore, the anti-immunoglobulin antibodies of the invention include antibodies against immunoglobulins or immunoglobulin fragments, such as Fab, Fv, F(ab)$_2$, etc.

Anti-immunoglobulin antibodies are generally made by injecting purified antibodies or fragments thereof into a distinct species. The antibodies are recognized as foreign antigens and elicit a strong humoral response. In this manner, anti-immunoglobulin antibodies are produced. However, generally, these anti-immunoglobulin antibodies are cross reactive with antibodies of other species. For example, in high-titer rabbit anti-mouse immunoglobulin serum, antibodies react with human antibodies.

The monoclonal antibodies of the present invention are selected such that they display minimal or no cross-reactivity with Ig of other species. Such highly selective monoclonal antibodies are obtained by rigorous screening of the monoclonal antibodies prepared. The monoclonal antibodies obtained by hyperimmunization against an antibody are screened against antibodies from another species as an inhibitor. For example, antimouse antibodies prepared in rats can be screened by utilizing human antibodies as inhibitors. In this manner, only monoclonal antibodies that bind to mouse antibody and not to human antibody are obtained.

While the invention is generally drawn to antibodies, more particularly monoclonal antibodies, it is recognized that antibody fragments, such as Fv, Fab, F(ab)$_2$ etc. which are capable of binding antigen can be utilized.

A key in identifying high-affinity, species-specific secondary antibodies is the rigorous screening process. In the first step, wells of a microtiter plate are coated with a moderately species-specific anti-mouse antibody. This antibody "captures" the rat monoclonal from hybridoma supernatant. Then the captured rat antibody is mixed with $^{125}$I (or otherwise suitably labelled) mouse Ig in subnanomolar quantities together with human antibody (or other species antibody) as inhibitor at ~10 mg/ml (~$10^{-4}$) concentration. This process selects for MAbs displaying a 100,000 or more fold greater binding to mouse than human (or other species) antibody.

The high affinity monoclonal antibodies of the invention can generally be made for immunoglobulins of any animal species. However, it is recognized that mice are the species from which most monoclonal antibodies have been derived. Thus, the invention finds particular use in the development of high affinity antimouse Ig antibodies.

The monoclonal antibodies of the invention are characterized by high affinity to the antigert binding fragments of the antibody utilized for immunization. Furthermore, the high affinity monoclonal antibodies display minimal or no cross reactivity with immunoglobulins from other species. Generally, the monoclonal antibodies of the invention have affinities for the particular species Fab ranging from about $1 \times 10^8$ to $1 \times 10^9 M^{-1}$, more generally from about $5 \times 10^7$ to about $5 \times 10^{11} M^{-1}$. These MAbs are considered to be completely species specific for antibody of a particular species if they show no significant binding to another species immunoglobulin at the concentration that it is normally present in serum.

Standard reference works setting forth the general principles of immunology include the work of Klein, J. Immunology: The Science of Cell-Noncell Discrimination (John Wiley & Sons, New York (1982)); Kennett et al., Monoclonal Antibodies, Hybridoma: A New Dimension in Biological Analyses, Plenum Press, New York (1980); Campbell, A. "Monoclonal Antibody Technology" In Laboratory Techniques in Biochemistry and Molecular Biology 13 (Burdon et al. eds., Elsevier, Amsterdam (1984)); and Eisen, H. N., In Microbiology, 3rd Ed., Davis et al., Harper & Row, Philadelphia (1980)).

Monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et. al. In Monoclonal Antibodies and T-Cell Hybridomas:563–681, Elsevier, N.Y. (1981)). Antibodies can also be produced by screening combinatorial libraries. See, for example, Davis et al. Biotechnology 9:165–169 (1991); Buchner and Rudolph, Biotechnology 9:157–162 (1991); Harlow and Lane, Antibodies, A Laboratory Manual, Cold Spring Harbor Laboratory, Cold Spring Harbor, N.Y. (1988) and the references cited therein.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, paramagnetic and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable enzymes or proteins with therapeutic application include tissue plasminogen activators, urinary type plasminogen activator, streptokinase, activated protein C, etc.

Examples of suitable radioisotopic labels include $^3$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Paramagnetic isotopes for purposes of in vivo diagnosis can also be used according to the methods of this invention. Examples of elements that are particularly useful for use in Magnetic Resonance Energy techniques include $^{157}$Gd, $^{55}$Mn, $^{162}$Dy, $^{52}$Cr, $^{56}$Fe, $^{123}$I, and the like. For discussion on in vivo nuclear magnetic resonance imaging, see, for example, Schaefer et al., JACC 14:472–480 (1989); Shreve et al., Magn. Reson. Med. 3:336-340 (1986); Wolf, G. L., Physiol. Chem. Phys. Med. NMR 16:93–95 (1984); Wesbey et al., Physiol. Chem. Phys. Med. NMR 16:145–155 (1984); Runge et al., Invest. Radiol. 19:408–415 (1984).

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., Clin. Chim. Acta 70:1-31 (1976), and Schurs et al., Clin. Chim. Acta 81:1–40 (1977)). Coupling techniques mentioned in the latter are the glutaraldehyde method, the periodate method, the dimaleimide method, the m-maleimidobenzxyl-N-hydroxy-succinimide ester method.

The detection of the antibodies (or fragments of antibodies) of the present invention can be improved through the use of carriers. Well known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. Those skilled in the art will note many other suitable carriers for binding monoclonal antibody, or will be able to ascertain the same by use of routine experimentation.

The monoclonal antibodies of the invention are useful in a wide variety of biological systems both in vitro and in vivo. Examples of potential in vitro uses include studying the binding, specificity and affinity of primary monoclonal antibodies in biological fluids containing other animal immunoglobulins. These could include, but are not limited to radioimmunoassays (RIA), radioallergosorbent test (RAST), radio-immunosorbent test (RIST), enzyme immunoassays (EIA), enzyme-linked immunosorbent assays (ELISA), antibody purification, imaging, cellular binding assays, cell sorting, histopathology, and the like. The antibodies may also be used as a labelling agent for detecting or measuring proteins or haptens. They may also be used to immunoprecipitate, immunodeplete, or immunopurify desired antigens from biological fluids.

The monoclonal antibodies of the invention find particular use in in vivo studies. Until the present invention the problem of crossreactivity has prevented effective use of a second antibody system for studying primary monoclonal antibodies in animals. These antibodies may be used as a diagnostic agent to detect bound primary antibodies which are directed against antigens of medical significance (such as blood clots, tumors, infections). They may also be used to target or direct medical treatments to targets defined by any primary antibody. They may be used to remove toxins or infectious agents from the blood.

It is contemplated that the antibodies of the present invention will be administered to an individual in therapeutically effective amounts. That is, in an amount sufficient to target the immunoglobulin of interest. The effective amount of the anti-Ig antibodies will vary according to the weight, sex, age and medical history of the individual. Other factors which influence the effective amount may include, but are not limited to the target immunoglobulin, nature and function of the particular therapeutic method, etc. Generally, the antibodies of the present invention will be administered in doses ranging from about 100 μg/kg body weight to about 1 μg/kg body weight, more generally about 10 μg/kg body weight to about 100 μg/kg body weight.

The compositions of the invention may be provided to a patient by means well-known in the art. Such means of introduction include oral, intranasal, subcutaneous, intramuscular, intravenous, intraarterial or parenteral means.

The antibodies of the invention are suited for the preparation of a kit. Such a kit may comprise a carrier means being compartmentalized to receive in close confinement one or more container means, each of said container means comprising the separate elements of the assay to be used.

The following experiments are offered by way of illustration not by way of limitation.

EXPERIMENTAL

In our research we have had to evaluate the performance of monoclonal antibodies in assays containing human or rabbit plasma. The high concentrations of human or rabbit antibody present in these plasmas has crossreacted with the second antibody probes and inhibited their binding to the mouse monoclonal antibody. Thus more complex and laborious experimental protocols have had to be designed. To circumvent this difficulty we sought to obtain high affinity, monoclonal rat anti-(mouse-Fab) antibodies which would not significantly bind to human or rabbit antibodies at the concentrations present in plasma. In this report we characterized several rat monoclonal antibodies (MAb) that bind to the κ chain of mouse immunoglobulin and show little or no binding inhibition by human or rabbit immunoglobulin.

Materials and Methods

Materials were obtained from the following suppliers: MAb 187.1 (rat anti-mouse κ chain, ATCC deposit number MB 58 (Yelton et al., Hybridoma 1:5–11 (1981)), American Type Culture Collection, (Rockville, Md.); affinity purified goat anti-(Fc fragment of rat Ig) (GAR) and iodogen, Pierce (Rockford, Ill.); Fab'2 fragments of mouse Ig, Cappel Laboratories (Malvern, Pa.); prestained protein standards and DEAE Affigel Blue, BioRad (Richmond, Calif.); Balb/C mice and New Zealand white rabbits, Charles River (Wilmington, Mass.); Fruend's adjuvant, Difco (Detroit, Mich.); $Na^{125}I$ Amersham (Arlington Heights, Ill.); polyvinylidene difluoride transfer membranes, Millipore (Bedford, Mass.); mercuripapain and RIA-grade bovine serum albumin Sigma (St. Louis, Mo.), DE52 resin, Whatman (Kent, England). All other chemicals were of reagent grade or better.

Monoclonal Antibody Production. One month old female CD rats were immunized subcutaneously with 60 μg of mouse Fab'2 and boosted two weeks later. Three days prior to fusion the rats were hyperimmunized with 500 μg of mouse Fab'2 intraperitoneally, followed by the same dose intravenously 2 days before fusion. Spleen cells were harvested from one rat and fused with mouse SP2/0 cells in a ratio of 1:1.6. The fusion was performed as described (Reed et al., Proc. Natl. Acad. Sci. USA 87:1114–1118 (1990)). Hybridomas producing antibody to mouse Fab'2 were identified by a solid-phase RIA. Wells of a microtiter plate were coated with 25 μl of mouse Fab'2 (3 μg/ml) for 3 hrs and then blocked with 1% bovine serum albumin (BSA). Hybridoma supernatants (25 μl) were then added to the wells for 1 hr. After thorough washing, bound antibody was detected by adding 25 μl (50,000 cpm) of $^{125}I$-goat anti-rat antibody (GAR) to each well for 1 hr. The GAR had been iodinated by the Iodogen method (Fraker et al., Biochem. Biophys. Res. Commun. 80:849–857 (1978)). The radioactivity was removed, the plates were washed, cut and the wells were γ-counted in Micro Medics counter. Of the 1740 wells assayed, 2.1% produced antibody yielding counts greater than 8 times background. These 60 hybridomas were then tested to determine if human antibody inhibited their binding to mouse Fab'2. The same assay was performed as above except that 25 μl of hybridoma supernatant was mixed with 100 μl of human or rabbit plasma (1 mM EDTA) and 25 μl of the mixture was added to the plates coated with mouse Fab'2. Bound rat antibody was detected by $^{125}$I-GAR. Hybridomas showing no significant inhibition by the antibody in plasma were subcloned by limiting dilution and their isotype was determined using Zymed reagents.

Mouse MAb purification and fragmentation. MAb RWR ($\gamma$1$\kappa$ isotype, (Reed et al., Proc. Natl. Acad. Sci. USA 87:1114–1118 (1990)) was expanded into ascites in mice that had been primed with 0.5 ml of pristane. Ascites were fractionated by precipitation with 40% ammonium sulfate. The precipitate was isolated by centrifugation at 17,000 rpm for 30 min at 4° C. The pellet was resuspended in approximately 20% of the initial volume with 0.9% saline and dialyzed into 10 mM sodium phosphate buffer, pH 7.4. After dialysis, the solution was clarified by repeat centrifugation at 17,000 for 30 min at 4° C. The supernatant was then passed over a 100 ml DEAE Affigel-Blue column at about 50–75 cc/hr. The bound antibody was eluted by a NaCl gradient of 0–100 mM NaCl in 10 mM phosphate, pH 7.4. Fractions containing antibody were identified by SDS-PAGE and concentrated under pressurized nitrogen gas using an Amicon concentrator. Fab fragments of RWR were prepared by limited papain digestion of whole MAb. Whole MAb was dialyzed into 0.1M NaH2PO4, 2 mM EDTA, pH 7.0. Cysteine MCl and papain were added to final concentrations of 0.1M and 1% (of MAb concentration) respectively. After an experiment had revealed the optimal time for papain digestion at 37° C., a preparative digest was performed. The digest was terminated by the addition of iodoacetamide to a final concentration of 1 mg/ml and the digest was dialyzed against 5 mM sodium phosphate, 0.02% NaN3. The digest was passed over a DE52 column which had previously been equilibrated with the same buffer. Fab was collected in the fall-through and whole IgG and Fc fragments were eluted by increasing sodium phosphate concentrations. The results of the digest and the subsequent purification were ascertained by SDS-PAGE (Laemmli, U.K., Nature 227:680–685 (1970)). Fab was radioiodinated by the Iodogen method (Fraker et at., Biochem. Biophys. Res. Commun. 80:849–857 (1978)). The specific radioactivity was determined in triplicate to be $5.01 \times 10^6$ cpm/pmol.

Equilibrium binding assays. To estimate the affinity of the rat monoclonal antibodies equilibrium binding assays were performed with $^{125}$I-mouse Fab. Dilution studies were performed to determine the appropriate concentration of rat MAb for assay. Wells of a microtiter plate were coated with GAR (25 $\mu$l, 3 $\mu$g/ml). Hybridoma culture supernatants (25 $\mu$l) were incubated with $^{125}$I-GAR (25 $\mu$l, 100,000 cpm) for 1 hr at room temperature. The mixtures were then placed at 4° C. for 0.5 hrs and then 40 $\mu$l samples were added to the wells of microtiter plates coated with GAR to immunoprecipitate the rat MAb. After 3 hrs of incubation at 4° C., the wells were washed, cut and $\gamma$-counted. These studies indicated that dilutions of hybridoma supernatants of 100 to 1000-fold were appropriate initial concentrations for binding studies. The dilution of supernatant was further adjusted as indicated by an analysis of the binding studies to obtain an antibody concentration below the $K_d$ (Schwarz, K. R., "The Principles of receptor binding studies" in H. A. Fozzard, et al., The Heart and Cardiovascular System 169–188 (Raven Press, New York) (1986)). Subsequently binding studies were performed in this manner except that the amount of $^{125}$I-mouse Fab was varied between $1.5 \times 10^6$ and $9 \times 10^3$ cpm to achieve Fab concentrations above and below the $K_d$. Background or nonspecific binding was estimated by performing the experiments in parallel using an inert control MAb 40-160 (Mudgett-Hunter et al., Mol. Immunol. 22:477–488 (1985)) and was less than 1%. Binding data were analyzed by the Ligand program (Munson et al., Anal. Biochem. 107:220–239 (1980)) as written for microcomputers with an MS-DOS operating system (McPherson, G. A. Kinetic, EBDA, Ligand Biosoft (Lowry) Cambridge, U.K. (1985)).

Inhibition assays. Wells of a microtiter plate were coated with 25 $\mu$l of GAR (3 $\mu$g/ml) for 2.5 hrs. Subsequently the GAR was removed and the nonspecific protein binding sites were blocked by incubation with 1% BSA in Tris-buffered saline with 0.02% azide (TBSA) for 1 hr. The BSA solution was removed and the plates were incubated with 25 $\mu$l of rat MAb for 1 hr. During this time, various dilutions of human or rabbit plasma (1 mM EDTA) were mixed with trace amounts of $^{125}$I mouse Fab (50,000 cpm/25 $\mu$l). Fab is the mouse antigen used in the generation of rat monoclonal antibodies. Non-mouse antibodies potentially competing for binding to the immobilized rat monoclonals are present in the plasma. The plates were washed to remove the unbound rat MAb and the different dilutions of plasma containing $^{125}$I-mouse Fab were added to the wells. After one hour of incubation, the wells were washed, cut and counted. Background was determined by the amount of cpm bound to the wells in the presence of greater than a 100-fold molar excess of cold mouse antibody. The concentration of immunoglobulin in the human and plasmas was assumed to be 10 mg/ml. After correcting for background, the percent inhibition of binding due to human or rabbit plasma was determined by the ratio of the amount of $^{125}$I-mouse Fab bound in the presence of the plasma dilution, to the amount bound in presence of no plasma.

Competitive epitope analysis. Rat MAbs were affinity purified from approximately 200 ml of culture media. The culture media was passed over separate 1 ml columns containing mouse monoclonal antibody RWR (isotype $\gamma$1$\kappa$) (Reed et al., Proc. Natl. Acad. Sci. USA 87:1114–1118 (1990)) coupled to Sepharose at a concentration of 2 mg/ml. The column was washed with TBSA, followed by TBSA with 0.5M NaCl until the $A_{280}$ was less than 0.05. Then the rat MAb was eluted with 0.1M glycine, pH 2.8 into tubes containing 0.5 ml of 1.0M Tris pH 9.1 which was added to neutralize the eluate. The wells of a microtiter plate were coated with 50 $\mu$l (25 $\mu$g/ml) of the affinity purified MAb for 2 hrs. The plates were washed and the nonspecific protein binding sites were then blocked by incubation with 1% BSA for 1 hr. The BSA solution was removed and 25 $\mu$l of each MAb culture media, as an inhibitor, was added to the wells followed by 25 $\mu$l of $^{125}$I-mouse Fab (200,000) cpm. Culture media from a $\kappa$ chain producing hybridoma ("kappa", a heavy chain loss variant of MAb 26-10 (Mudgett-Hunter et al., Mol. Immunol. 22:477–488 (1985)) was also added as an inhibitor. After 1 hr of incubation, the wells were aspirated, thoroughly washed, cut and $\gamma$-counted. The percent maximal binding was determined as 100 times the quotient of the cpm of $^{125}$I-Fab bound in the presence of a given MAb divided by that obtained in the absence of any inhibitor.

Immunoblotting. Whole mouse MAb, or Fab fragments thereof were mixed with sample buffer with or without $\beta$-mercaptoethanol and electrophoresed on 12% polyacrylamide gels as described (Laemmli, U.K.

Nature 227:680–685 (1970)). Proteins were electrophoretically transferred to polyvinylidene difluoride membranes using a semi-dry technique (Khyse-Anderson, J., J. Biochem. Biophys. Meth. 10:203–209 (1984)). Protein transfer was verified by India ink staining. The nitrocellulose was incubated for 30 min. in 1% BSA to block the nonspecific protein binding sites. The blots were washed and incubated in rat MAb culture media for 1 hr. After washing 3 times in TBSA for 5 min. intervals, the blots were incubated with $^{125}$I-GAR ($1\times 10^6$ cpm) for 1 hr. The radioactivity was removed and the blots were washed 3 times for 5 min. intervals. After drying, the nitrocellulose sheets were subjected to autoradiography to detect bound antibody.

Results

From the somatic cell fusion of immunized rat splenocytes with mouse SP2/0 cells, 60 hybridomas were identified as producing antibody which bound to polyclonal mouse Fab'2 fragments at greater than or equal to 8 times background. These hybridomas were then tested to see if their binding to mouse Fab was inhibited by human antibody in human plasma. Four hybridomas appeared to show little or no inhibition and were cloned by limiting dilution.

Figure 1B:
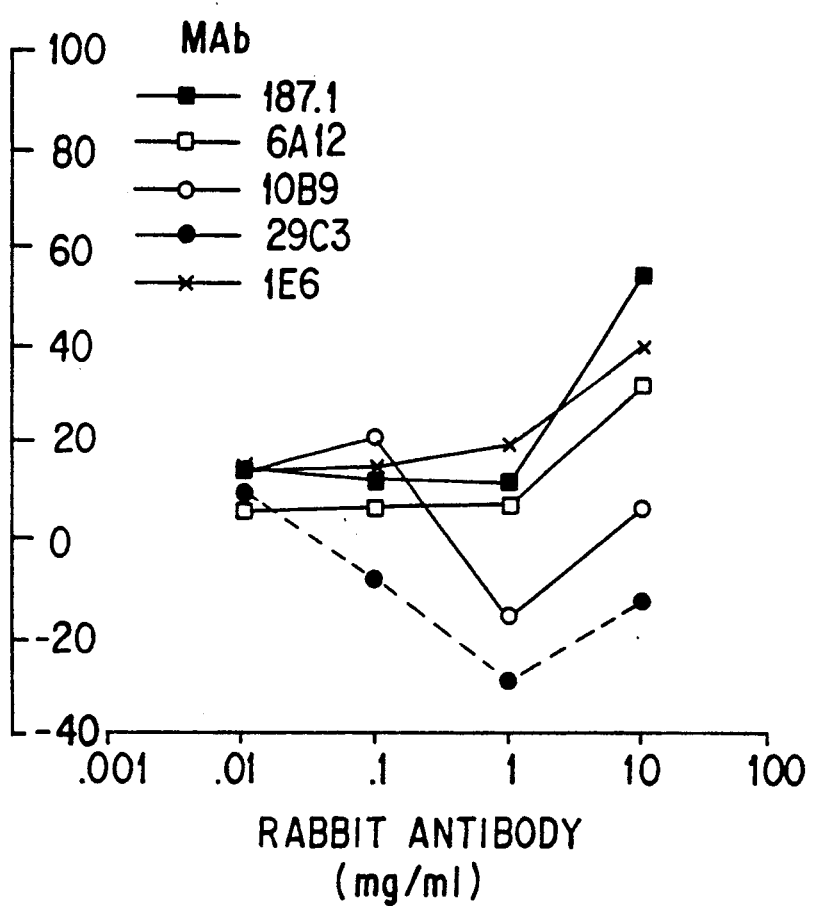

After subcloning, these MAbs were more extensively tested to determine whether their binding was inhibited by human or rabbit antibody in plasma (FIGS. 1A and 1B). A previously reported rat anti-(mouse κ chain) MAb, 187.1 (Yelton et at., Hybridoma 1:5–11 (1981)) was used as a control. FIG. 1A shows that MAb 187.1 was more than 80% inhibited by the high concentrations of human antibody found in plasma. MAbs 1E6 and 6A12 show mild inhibition (<30%) by human antibody, and MAbs 29C3 and 10B9 show little, if any, inhibition by plasma levels of human antibody. Nonspecific binding in this assay was estimated by using cold mouse MAb and was approximately 1%. When a similar assay was performed with rabbit antibody (in rabbit plasma), a similar, though less marked pattern of inhibition was seen. FIG. 1B shows that MAbs 187.1, 1E6, and 6A12 were moderately inhibited by rabbit antibody, but MAbs 29C3 and 10B9 were not.

Liquid-phase, equilibrium binding assays were performed to estimate the relative affinities of these MAbs for mouse Fab. For comparison the affinity of 187.1 was measured and found to be $4.28\times 10^8 M^{-1}$. The affinities of the other rat MAbs were equal to, or nearly 10-fold higher than, 187.1 ($4.34\times 10^8$ to $4.11\times 10^9$). The heavy chain isotypes of all MAbs was γ2c. the light chain were all of the κ serotypes, except for 1E6 which was a λ serotype.

Figure 2:
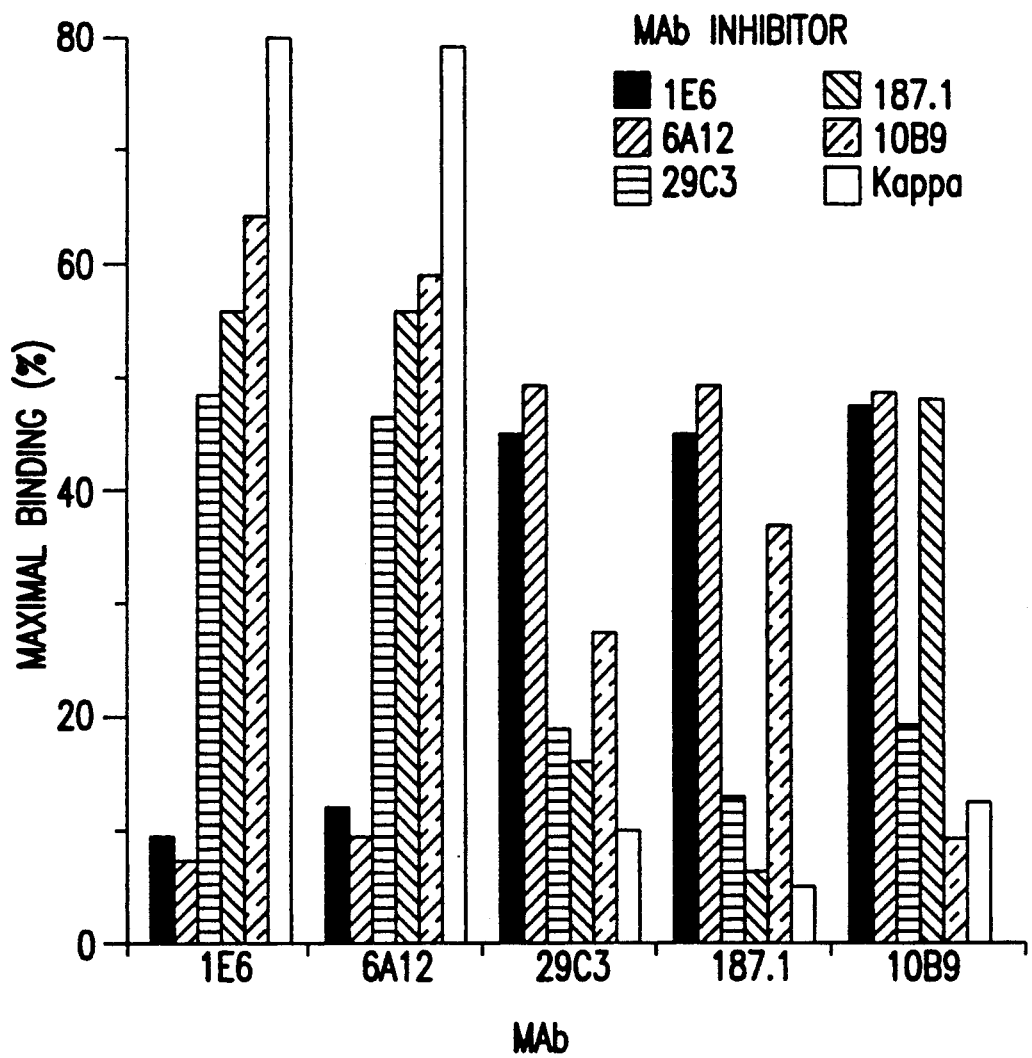
FIG. 2. Comparative binding analysis of rat MAbs to mouse Fab. Rat MAbs were immobilized in the wells of a microtiter plate. Then $^{125}$I mouse Fab was mixed separately with hybridoma supernatants from each of the rat MAbs. The resulting amount of inhibition of binding of the $^{125}$I-mouse Fab to the immobilized rat MAb was computed. On the abscissa is shown the immobilized MAb; the bars represent the percent of inhibition of binding of the $^{125}$I-mouse Fab to the immobilized MAb by various hybridoma supernatants.

To determine whether the MAbs bound to similar epitopes, a competitive binding study was performed. MAbs were immobilized in the wells of microtiter plates. Then trace amounts of $^{125}$I-mouse Fab were separately mixed with hybridoma culture supernatants containing each rat MAb, or a κ light chain mouse MAb, as an inhibitor and added to wells containing the immobilized rat MAb. The amount that each MAb in solution inhibited the binding of the $^{125}$-mouse Fab to each immobilized MAb was computed and is shown in the bars in FIG. 2. Three inhibition patterns emerged suggesting that the MAbs recognized three different epitopes. A distinct epitope appeared to be recognized by MAbs 1E6 and 6A12. These MAbs strongly inhibited each other but were not inhibited by free κ chain and were only moderately inhibited by the other MAbs. Although they were not inhibited by free κ chain in solution, other binding experiments demonstrated that these MAbs bind κ chain when it is associated with heavy chain but did not recognize mouse immunoglobulin with λ light chains (data not shown). A second epitope appears to be recognized by MAbs 29C3 and 187.1. These MAbs were strongly inhibited by each other and by κ chain. They were less strongly inhibited by 10B9 and even less affected by MAbs 1E6 and 6A12. A third, but related epitope appeared to be recognized by 10B9. This MAb was strongly inhibited by κ chain and MAb 29C3. It was weakly inhibited by MAbs 1E6, 6A12, and 187.1.

Figure 3:
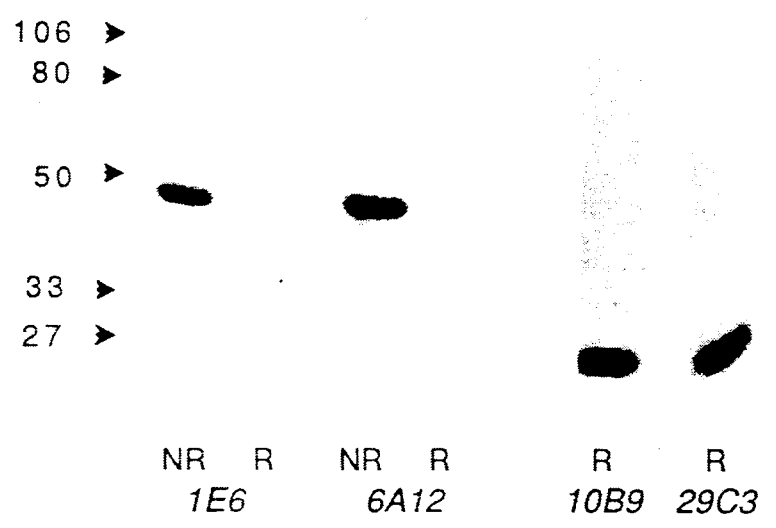

Immunoblotting experiments were performed to further analyze the binding specificity of these MAbs for denatured and reduced mouse immunoglobulins. FIG. 3 shows the results. MAbs 187.1, 10B9, and 29C3 all bound well to the fully reduced κ chain. However, MAbs 1E6 and 6A12 bound to SDS-denatured Fab but did not bind well to the SDS-treated and reduced Fab.

The hybridoma cell line producing antibody 10B9 has been deposited with the American Type Culture Collection (ATCC), 12301 Parklawn Drive, Rockville, Md. 20852-1776. The deposit number of the cells is CRL 10946.

Discussion

To obtain a specific probe for mouse antibody in human or rabbit plasma, we have generated a panel of rat MAbs that bind to the κ-chain of mouse Fab and show minimal or no crossreactivity with human or rabbit IgG. These MAbs were generated against polyclonal mouse Fab'2 but appear to react primarily with the κ-chain of mouse antibody, either when it is free or complexed with heavy chain. By competition binding and immunoblotting studies it appears that the MAbs bind to three epitopes. The first major epitope is conformationally dependent and is recognized by MAbs 6A12 and 1E6. These two antibodies mutually inhibit the binding of each other, they do not bind to free κ light chain in solution and do not bind to reduced mouse antibody. They appear to recognize an epitope in the Fab fragment of mouse immunoglobulin that is present only when heavy chain and a κ light chain are associated together. The second major epitope is recognized by MAbs 29C3 and 187.1. This epitope is present on free κ-chain in solution and still present on fully reduced and denatured κ-chain in immunoblots. These MAbs strongly inhibit the binding of each other but have little effect on the binding of 1E6 or 6A12. The third epitope is recognized by MAb 10B9 and appears close to, but distinct from, the epitope recognized by 187.1 and 29C3. Like these two MAbs, 10B9 recognizes free κ-light chain in solution and when it is fully denatured and reduced.

Unlike 29C3 however, the binding of this MAb to mouse Fab is poorly inhibited by 187.1, suggesting that its binding site only minimally overlaps.

Rat MAbs that bind to mouse IgG have been reported (Yelton et al., Hybridoma 1:5–11 (1981)). The best characterized of these is MAb 187.1. This MAb has been shown to be useful in solid-phase immunoprecipitation studies (Ware et al., J. Immunol. Methods 74:93–104 (1984)). Its reported avidity for whole mouse immunoglobulin was $2\times 10^9 M^{-1}$ in a solid phase radio-immunoassay (Ware et at., supra). Our estimates of the affinity of MAb 187.1 for mouse Fab in a liquid phase assay were lower but are consistent with the differences known to exist between assays designed to measure avidity and affinity (Stevens et at., J. Immunol. 137:1937–1944 (1986)). The MAbs reported herein display affinities ranging from approximately equal to 10-fold greater than that noted for MAb 187.1. Like MAb 187. these MAbs recognize κ-chain of mouse Ig which is present on over that 95% of mouse immunoglobulin. These MAbs also differ in heavy chain isotype, being exclusively of the γ2c serotype. Most importantly, these MAbs show substantially less, or no crossreactive binding to human or rabbit immunoglobulin at the concentrations which are present in plasma.

Species-specific, high affinity, MAbs like these will be useful tools for mouse antibody detection, immunoprecipitation, MAb screening, or targeting in complex biological fluids in vitro. They may also be useful for studying the binding and effects of mouse MAbs in vivo.

TABLE I

| MAb | Affinity Constant ($M^{-1}$) | Dissociation Constant (M) |
|---|---|---|
| 187.1 | $4.28 \pm 0.27 \times 10^8$ | $2.34 \times 10^{-9}$ |
| 29C3 | $4.34 \pm 0.35 \times 10^8$ | $2.30 \times 10^{-9}$ |
| 10B9 | $2.18 \pm 0.21 \times 10^9$ | $4.59 \times 10^{-10}$ |
| 1E6 | $2.62 \pm 0.29 \times 10^9$ | $3.82 \times 10^{-10}$ |
| 6A12 | $4.11 \pm 0.52 \times 10^9$ | $2.43 \times 10^{-10}$ |

Table 1. Affinities of rat MAbs for mouse Fab. Equilibrium solution binding assays were performed to estimate the affinity of rat MAbs. In these assays MAb concentration was less than the $K_d$ and the mouse Fab was varied to achieve concentrations above and below the $K_d$ (Schwarz, K. R., "The Principles of Receptor Binding Studies" in H. A. Fozzard, et al., The Heart and Cardiovascular System 169–188 (Raven Press, New York) (1986)). The binding data was analyzed through the use of the Ligand program (Munson et al., Anal. Biochem. 107:220–239 (1980; McPherson, G. A., Kinetic, EBDA, Ligand Biosoft (Lowry) Cambridge, U.K. (1985).

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for screening a hybridoma supernatant for monoclonal antibodies which are completely species specific for the immunoglobulin of a first species (hereinafter "S1-Ig") comprising:
   (a) incubating said supernatant with S1-Ig and immunoglobulin from a second species (hereinafter "S2-Ig") wherein,
      (i) the concentration of S2-Ig is at least 100,000 times greater than the concentration of S1Ig; and
      (ii) the concentration of S2-Ig is equal to or greater than the concentration normally found in the serum of said second species;
   (b) after the incubation of step (a), quantitating the amount of S1-Ig bound by antibody; and
   (c) selecting those supernatants having antibodies which bind S1-Ig despite the presence of S2-Ig.

2. The method of claim 1, wherein S2-Ig is human immunoglobulin.

3. The method of claim 1, wherein S 1-Ig is murine immunoglobulin.

4. The method of claim 1, wherein S 1-Ig is murine immunoglobulin and S2-Ig is human immunoglobulin.

5. Antibody 10B9 (ATCC deposit No. CRL 10946).

* * * * *